United States Patent

Zasloff et al.

[11] Patent Number: 5,225,399
[45] Date of Patent: Jul. 6, 1993

[54] ANTIMICROBIAL AMPHIPHILIC PEPTIDES

[75] Inventors: Michael Zasloff, Merion Station; W. Lee Maloy, Lansdale; U. Prasad Kari, Lansdale; Michael Brasseur, Lansdale, all of Pa.

[73] Assignee: The Children's Hospital of Philadelphia, Philadelphia, Pa.

[21] Appl. No.: 686,116

[22] Filed: Apr. 15, 1991

[51] Int. Cl.$^5$ .................. A61K 37/02; C07K 7/08
[52] U.S. Cl. .................................... 514/13; 530/326
[58] Field of Search ...................... 514/13; 530/326

[56] References Cited

U.S. PATENT DOCUMENTS 4,507,230 3/1985 Tam et al.
4,962,277 10/1990 Cuervo et al.

Primary Examiner—Lester L. Lee
Attorney, Agent, or Firm—Woodcock Washburn Kurtz Mackiewicz & Norris

[57] ABSTRACT

A biologically active peptide which includes the following structure:

$$R_1-R_1-R_1-R_4-R_1-R_1-R_2-R_1-R_1-R_1-R_1-R_1-R_1-R_{1a}-R_1-R_1-R_3-R_2R_2-R_{1a}$$

$R_1$ and $R_{1a}$ are hydrophobic amino acids, $R_2$ is a basic hydrophilic amino acid, $R_3$ is a neutral hydrophilic amino acid, and $R_4$ is hydrophobic or basic hydrophilic amino acid. Preferably, $R_{1a}$ is cysteine.

Examples of peptides have the following structural formulae:
(SEQ ID NO:1);
(SEQ ID NO:2);
(SEQ ID NO:3);
(SEQ ID NO:4);
(SEQ ID NO:5); and
(SEQ ID NO:6).

The peptide may be employed in a pharmaceutical composition.

2 Claims, No Drawings

ANTIMICROBIAL AMPHIPHILIC PEPTIDES

This invention relates to biologically active peptides, and more particularly to novel biologically active peptides and uses therefor.

In accordance with an aspect of the present invention, there is provided a biologically active amphiphilic peptide including the following basic structure:

$$R_1\text{-}R_1\text{-}R_1\text{-}R_4\text{-}R_1\text{-}R_1\text{-}R_2\text{-}R_1\text{-}R_1\text{-}R_1\text{-}R_1\text{-}R_1\text{-}R_{1a}\text{-}R_1\text{-}R_1\text{-}R_3\text{-}R_2R_2\text{-}R_{1a}$$

wherein $R_1$ and $R_{1a}$ are hydrophobic amino acids, $R_2$ is a basic hydrophilic amino acid, $R_3$ is a neutral hydrophilic amino acid, and $R_4$ is hydrophobic or basic hydrophilic amino acid. Preferably, $R_{1a}$ is cysteine.

The hydrophobic amino acids include but are not limited to Ala,Cys,Phe,Gly,Ile,Leu,Met,Pro,Val,Trp,Tyr, norleucine (Nle), norvaline (Nva), and cyclohexylalanine (Cha).

The basic hydrophilic amino acids include but are not limited to Lys,Arg,His, Orn, homoarginine (Har), 2-4-diamino butyric acid (Dbu), and p-aminophenylalanine.

The neutral hydrophilic amino acids include but are not limited to Asn,Gln,Ser, and Thr.

A representative example of the peptides of the present invention is found in tadpoles of the American bullfrog Rana catesbiana and is of the following structural formula as indicated in the accompanying sequence listing:

SEQ ID NO:1)

Further representative examples of the peptides of the present invention are derivatives of the above-mentioned peptide, and are of the following structural formulae as indicated in the accompanying sequence listing:

(SEQ ID NO:2)
(SEQ ID NO:3)
(SEQ ID NO:4)
(SEQ ID NO:5)
(SEQ ID NO:6)

Each of the above-mentioned peptides, (SEQ ID NO:1) through (SEQ ID NO:6), includes a disulfide (S—S) bond between residues $Cys^{14}$ and $Cys^{20}$.

In general, the peptides of the present invention are ion channel-forming peptides.

An ion channel-forming peptide or protein or ionophore is a peptide or protein which increases the permeability for ions across a natural or synthetic lipid membrane. B. Christensen et al. PNAS Vol. 85 Pgs. 5072-76 (July, 1988) describes methodology which indicates whether or not a peptide or protein has ion channel-forming properties and is therefore an ionophore. As used herein an ion channel-forming peptide or ion channel-forming protein is a peptide or protein which has ion channel-forming properties as determined by the method of Christensen et al.

In accordance with one embodiment, each of the amino acid residues is a D-amino acid residue or glycine. Although the scope of this particular embodiment is not to be limited to any theoretical reasoning, it is believed that the above-mentioned peptides, when consisting entirely of D-amino acid or glycine residues, may have increased resistance to proteolytic enzymes while retaining their biological activity. Such peptides thus may be administered orally. Also, in accordance with another embodiment, all of the amino acid residues are either D-amino acid residues or glycine, or L-amino acid residues or glycine.

An amphiphilic peptide is a peptide which includes both hydrophobic and hydrophilic peptide regions.

In general, the peptides hereinabove described, and/or analogues or derivatives thereof are generally water soluble to a concentration of at least 20 mg/ml at neutral pH in water. In addition, the structure of such peptides provides for flexibility of the peptide molecule. When the peptide is placed in water, it does not assume an amphiphilic structure. When the peptide encounters an oily surface or membrane, the peptide chain folds upon itself into a rod-like structure.

The peptides and/or analogues or derivatives thereof, may be C-terminal acids or amides.

The peptides and/or analogues or derivatives thereof may be administered to a host; for example a human or non-human animal, in an amount effective to inhibit growth of a target cell, virus, or, virally-infected cell. Thus, for example, the peptides and/or analogues or derivatives thereof may be used as antimicrobial agents, anti-viral agents, antibiotics, anti-tumor agents, antiparasitic agents, antifungal agents, spermicides, as well as exhibiting other bioactive functions.

The term "antimicrobial" as used herein means that the peptides of the present invention inhibit, prevent, or destroy the growth or proliferation of microbes such as bacteria, fungi, or the like.

The term "antibiotic" as used herein means that the peptides employed in the present invention produce effects adverse to the normal biological functions of the non-host cell, tissue, or organism including death or destruction and prevention of the growth or proliferation of the non-host cell, tissue, or organism when contacted with the peptides.

The term "spermicidal" as used herein means that the peptides employed in the present invention, inhibit, prevent, or destroy the motility of sperm.

The term "antiviral" as used herein means that the peptides employed in the present invention inhibit, prevent, or destroy the growth or proliferation of viruses, or of virally-infected cells.

The term "anti-tumor" as used herein means that the peptide inhibits the growth of or destroys tumors.

The term "antifungal" as used herein means that the peptides of the present invention may be used to inhibit the growth of or destroy fungi.

The term "antiparasitic" as used herein means that the peptides of the present invention may be used to inhibit the growth of or destroy parasites.

The peptides of the present invention have a broad range of potent antibiotic activity against a plurality of microorganisms including Gram-positive and Gram-negative bacteria, fungi, protozoa, and the like, as well as parasites. The peptides of the present invention allow a method for treating or controlling microbial infection caused by organisms which are sensitive to the peptides. Such treatment may comprise administering to a host organism or tissue susceptible to or affiliated with a microbial infection an antimicrobial amount of at least one of the peptides.

Because of the antibiotic, antimicrobial, and antiviral properties of the peptides, they may also be used as preservatives or sterilants of materials susceptible to microbial or viral contamination.

The peptide and/or derivatives or analogues thereof may be administered in combination with a non-toxic pharmaceutical carrier or vehicle such as a filler, non-toxic buffer, or physiological saline solution. Such pharmaceutical compositions may be used topically or systemically and may be in any suitable form such as a liquid, solid, semi-solid, injectable solution, tablet, ointment, lotion, paste, capsule, or the like. The peptide compositions may also be used in combination with adjuvants, protein inhibitors, or compatible drugs where such a combination is seen to be desirable or advantageous in controlling infection caused by harmful microorganisms including protozoa, viruses, and the like, as well as by parasites.

The peptide(s) of the present invention may be administered to a host; in particular an animal, in an effective antibiotic and/or anti-tumor and/or anti-viral and/or anti-microbial and/or anti-parasitic and/or an antispermicidal amount.

Depending on the use, a composition in accordance with the invention will contain an effective antimicrobial amount and/or an effective antispermicidal amount and/or an effective anti-viral amount and/or an effective anti-tumor amount and/or an effective antibiotic amount and/or anti-parasitic amount of one or more of the hereinabove described peptides which have such activity.

The peptide of the present invention may also be employed in promoting or stimulating healing of a wound in a host.

The term "wound healing" as used herein includes various aspects of the would healing process.

These aspects include, but are not limited to, increased contraction of the wound, increased deposition of connective tissue, as evidenced by, for example, increased deposition of collagen in the wound, and increased tensile strength of the wound, i.e., the peptides increase wound breaking strength. The peptides of the present invention may also be employed so as to reverse the inhibition or depression of wound healing caused by steroids such as cortisone, or by conditions which may cause a depressed or compromised immune system.

The peptides of the present invention may be used in the treatment of external burns and to treat and/or prevent skin and burn infections. In particular, the peptides may be used to treat skin and burn infections caused by organisms such as, but not limited to, *P. aeruginosa* and *S. aureus*.

The peptides are also useful in the prevention or treatment of eye infections. Such infections may be caused by bacteria such as, but not limited to, *P. aeruginosa, S. aureus,* and *N. gonorrhoeae,* by fungi such as but not limited to *C. albicans* and *A. fumigatus,* by parasites such as but not limited to *A. castellani,* or by viruses.

The peptides may also be effective in killing cysts, spores, or trophozoites of infection - causing organisms. Such organisms include, but are not limited to Acanthamoeba which forms trophozoites or cysts, *C. albicans,* which forms spores, and *A. fumigatus,* which forms spores as well.

The peptides may also be administered to plants in an effective antimicrobial or antiviral or antiparasitic amount to prevent or treat microbial or viral or parasitic contamination thereof.

In general, the peptide is employed to provide peptide dosages of from 0.1 mg. to 500 mg. per kilogram of host weight. When administered topically, the peptide is used in a concentration of from 0.05% to 10%.

It is also to be understood that, within the scope of the present invention, the peptides may be employed in vitro or in vivo. The peptides may be administered directly to the target cell, virus, or virally-infected cell, or may be administered systemically.

The peptides may be produced by known techniques and obtained in substantially pure form. For example, the peptides may be synthesized on an automatic peptide synthesizer. *Journal of the American Chemical Society.* Vol. 85, pgs. 2149-54 (1963). It is also possible to produce such peptides by genetic engineering techniques.

In accordance with another embodiment, the peptides of the present invention may be employed in combination with a toxic ion for the purposes hereinabove described.

A toxic ion is one which when introduced into a target cell, virus, or virally-infected cell inhibits and/or prevents and/or destroys the growth of the target cell, virus, or virally-infected cell.

Such a toxic ion is one which in the absence of an ion channel forming peptide is unable to cross a natural or synthetic lipid membrane; in particular a cell membrane, in sufficient amounts to affect a cell adversely.

The peptide and toxic ion may be administered as a single composition or in separate compositions, and the single or separate compositions may include additional materials, actives and/or inactives, in addition to the peptide and toxic ion. As representative examples of toxic ions which may be employed, there may be mentioned fluoride, peroxide, bicarbonate, and silver, zinc, mercury, arsenic, copper, platinum, antimony, gold, thallium, nickel, selenium, bismuth, and cadmium ions.

The peptide and the toxic ion, whether administered or prepared in a single composition or in separate compositions, are employed in amounts effective to inhibit and/or prevent and/or destroy the growth of the target cell, virus, or virally-infected cell. In effect, the ion potentiates the action of the peptide, i.e., the amount of toxic ion is effective to reduce the maximum effective concentration of the peptide or protein for inhibiting growth of a target cell, virus, or virally-infected cell.

The toxic ion, when used topically, is generally employed in a concentration of from 0.05% to 2.0%. When used systemically, the ion is generally employed in an amount of from 1 to 10 mg. per kg. of host weight. Peptide dosages may be within the ranges hereinabove described.

It is also to be understood that the peptide and toxic ion may be delivered or administered in different forms; for example, the toxic ion may be administered orally, while the peptide may be administered by IV or IP.

As representative examples of administering the peptide or protein and toxic ion for topical or local administration, the peptide could be administered in an amount of up to about 1% weight to weight and the toxic ion delivered in an amount of about 50 mM (about 0.1%). Alternatively, the toxic ion, in the form of a salt such as sodium fluoride, could be administered orally in conjunction with systemic administration of the peptide. For example, the peptide may be administered IV or IP to achieve a serum dose of 100 micrograms per milliliter (10 milligrams per kilogram) in conjunction with an oral dose of toxic ion, in particular, sodium fluoride, of 10 meq per kilogram.

In accordance with another embodiment, the peptides of the present invention may be administered to a host in combination with an antibiotic selected from the class consisting of bacitracins, gramacidin, polymyxin, vancomycin, teichoplanin, aminoglycosides, hydrophobic antibiotics, penicillins, monobactams, or derivatives or analogues thereof.

The bacitracins, gramacidin, polymyxin, vancomycin, teichoplanin, and derivatives and analogues thereof, are a group of polypeptide antibiotics. A preferred bacitracin is bacitracin A.

Aminoglycoside antibiotics include tobramycin, kanamycin, amikacin, the gentamicins (e.g., gentamicin $C_1$, gentamicin $C_2$, gentamicin $C_{1a}$), netilmicin, kanamycin, and derivatives and analogues thereof. The preferred aminoglycosides are tobramycin and the gentamicins. The aminoglycosides, and the bacitracins hereinabove described, tend to be hydrophilic and water-soluble.

Penicillins which may be employed include, but are not limited to benzyl penicillin, ampicillin, methicillin (dimethoxyphenyl penicillin), ticaricillin, penicillin V (phenoxymethyl penicillin), oxacillin, cloxacillin, dicloxacillin, flucloxacillin, amoxicillin, and amidinocillin. Preferred penicillins which may be employed are benzyl penicillin and ampicillin. A preferred monobactam which may be employed is aztreonam.

As representative examples of hydrophobic antibiotics which may be used in the present invention, there may be mentioned macrolides such as erythromycin, roxythromycin, clarithromycin, etc.; 9-N-alkyl derivatives of erythromycin; midecamycin acetate; azithromycin; flurithromycin; rifabutin; rokitamycin; a 6-O-methyl erythromycin A known as TE-031 (Taisho); rifapentine; benzypiperazinyl rifamycins such as CGP-7040, CGP-5909, CGP-279353 (Ciba-Geigy); an erythromycin A derivative with a cyclic carbamate fused to the $C_{11}/C_{12}$ position of a macrolide ring known as A-62514 (Abbott); AC-7230 (Toyo Jozo); benzoxazinorifamycin; difficidin; dirithromycin; a 3-N-piperdinomethylzaino methyl rifamycin SV known as FCE-22250 (Farmitalia); M-119-a (Kirin Brewery); a 6-O-methyl-1-4″-O-carbamoyl erythromycin known as A-63075 (Abbott); 3-formylrifamycin SV-hydrazones with diazabicycloalkyl side chains such as CGP-27557 and CGP-2986 (Ciba-Geigy); and 16-membered macrolides having a 3-0-alpha-L-cladinosyl moiety, such as 3-0-alpha-L-cladinosyldeepoxy rosaramicin; tylosins and acyl demycinosyl tylosins.

In addition to the macrolides hereinabove described, rifamycin, carbenicillin, and nafcillin may be employed as well.

Other antibiotics which may be used (whether or not hydrophobic) are antibiotics which are 50-S ribosome inhibitors such as lincomycin; clindamycin; and chloramphenicol; etc.; antibiotics which have a large lipid like lactone ring, such as mystatin; pimaricin, etc.

The peptide and antibiotic may be adminstered by direct administration to a target cell or by systemic or topical administration to a host which includes the target cell, in order to prevent, destroy or inhibit the growth of a target cell. Target cells whose growth may be prevented, inhibited, or destroyed by the administration of the peptides and antibiotic include Gram-positive and Gram-negative bacteria as well as fungal cells.

The antibiotic, such as those hereinabove described, or derivatives or analogues thereof, when used topically, is generally employed in a concentration of about 0.1% to about 10%. When used systemically, the antibiotic or derivative or analogue thereof is generally employed in an amount of from 1.25 mg. to about 45 mg. per kg. of host weight per day. Peptide dosages may be those as hereinabove described.

As representative examples of administering the peptide and antibiotic for topical or local administration, the peptide could be admnistered in an amount of from about 0.1% to about 10% weight to weight, and the antibiotic is delivered in an amount of from about 0.1% to about 10% weight to weight.

In accordance with another embodiment, the peptides of the present invention may be administered in combination with an antiparasitic agent or an antifungal agent.

Antiparasitic agents which may be employed include, but are not limited to, anti-protozoan agents. Examples of specific anti-parasitic agents which may be employed include, but are not limited to, pentamidine isethionate, and propamidine isethionate (Brolene).

Anti-fungal agents which may be employed include, but are not limited to, ketoconazole. It is also to be understood that certain anti-parasitic agents, may also have anti-fungal activity, and that certain anti-fungal agents may have anti-parasitic activity.

In accordance with another embodiment, the peptides of the present invention may be administered in combination with an antibiotic which inhibits DNA gyrase, which is an enzyme involved in the formation of bonds between individual coiling strands of replicating bacterial DNA. Thus, DNA gyrase is necessary for the normal replication of bacterial DNA, and, therefore, antibiotics which inhibit DNA gyrase inhibit the normal replication of bacterial DNA.

Examples of antibiotics which inhibit DNA gyrase include nalidixic acid, oxolinic acid, cinoxacin, and quinolone antibiotics which include ciprofloxacin, norfloxacin, ofloxacin, enoxacin, pefloxacin, lomefloxacin, fleroxacin, tosulfloxacin, temafloxacin, and rufloxacin.

In accordance with another embodiment, the peptides of the present invention may be administered for the purpose hereinabove described in combination with other biologically active amphiphilic peptides, or in combination with ion channel-forming proteins.

The invention will now be further described with respect to the following examples; however, the scope of the present invention is not to be limited thereby.

EXAMPLE 1—ANTIBACTERIAL ASSAY

The procedure for the following antibacterial assay is based upon the guidelines of the National Committee for Clinical Laboratory Standards, Document M7-T2, Volume 8, No. 8, 1988.

Stock solutions of the following Peptides (1) through (6) in accordance with the present invention are prepared at a concentration of 512 μ/ml in sterile deionized distilled water and stored at −70° C.

Peptide 1 has the following structural formula: (SEQ ID NO:1)-OH.

Peptide 1A has the following structural formula: (SEQ ID NO:1)-NH₂

Peptide 2 has the following structural formula: (SEQ ID NO:2)-OH.

Peptide 3 has the following structural formula: (SEQ ID NO:3)-OH.

Peptide 4 has the following structural formula: (SEQ ID NO:4)-OH.

Peptide 5 has the following structural formula: (SEQ ID NO:5)-OH.

Peptide 6 has the following structural formula: (SEQ ID NO:6)-OH.

The stock peptide solution is diluted in serial dilutions (1:2) down the wells of a microtiter plate so that the final concentrations of peptides in the wells are 0.25, 0.50, 1, 2, 4, 8, 16, 32, 64, 128, and 256 μg/ml. $1-5\times10^5$ CFUs/ml of either *S. aureus* ATCC 25923, *E. coli* ATCC 25922, or *P. aeruginosa* ATCC 27853 were added to the wells in full strength Mueller Hinton broth (BBL 11443) from a mid-log culture. The inoculum is standarized spectrophotometrically at 600nm and is verified by colony counts. The plates are incubated for 16–20 hours at 37° C., and the minimal inhibitory concentration (MIC) for each peptide is determined. Minimal inhibitory concentration is defined as the lowest concentration of peptide which produces a clear well in the microtiter plate. The results are given in Table I below.

TABLE I

| Peptide | MIC (μg/ml) | | |
|---|---|---|---|
| | S. aureus | P. aeruginosa | E. coli |
| (1) | 4 | 128 | 64 |
| (1a) | 4 | 128 | 32 |
| (2) | 32 | 256 | 64 |
| (3) | 32 | 256 | 32 |
| (4) | 4 | >256 | 128 |
| (5) | 4 | 128 | 32,64 |
| (6) | 16 | 128 | 32,64 |

The peptides of the present invention, whether administered alone or in combination with agents such as toxic ions, antibiotics, or other biologically active peptides or proteins as hereinabove described, may be employed in a wide variety of pharmaceutical compositions in combination with a non-toxic pharmaceutical carrier or vehicle such as a filler, non-toxic buffer, or physiological saline solution. Such pharmaceutical compositions may be used topically or systemically and may be in any suitable form such as a liquid, solid, semi-solid, injectable solution, tablet, ointment, lotion, paste, capsule or the like. The peptide and/or agent as hereinabove described may also be used in combination with adjuvants, protease inhibitors, or compatible drugs where such a combination is seen to be desirable or advantageous in controlling infection caused by harmful microorganisms including protozoa, viruses, parasites, fungi, and the like.

The peptide may be administerd to a host in particular an animal, in an effective antibiotic and/or antitumor and/or antiviral and/or antimicrobial and/or antispermicidal and/or antifungal and/or antiparasitic amount, or in an amount effective to stimulate wound healing in a host. The peptides may be administerd either alone or in combination with a toxic ion, antibiotic, or ion channel forming peptide or protein as hereinabove described. When the peptide is administered in combination with a toxic ion, the activity of the peptide is potentiated.

When the peptide is administered in combination with an agent as hereinabove described, it is possible to administer the peptide and agent in separate forms. For example, the agent may be administered systemically and the peptide may be administered topically.

When the peptide is administered topically, it may be administered in combination with a water-soluble vehicle, said water-soluble vehicle being in the form of an ointment, cream, lotion, paste or the like. Examples of water-soluble vehicles which may be employed include, but are not limited to, glycols, such as polyethylene glycol, hydroxycellulose, and KY Jelly. The water-soluble vehicle is preferably free of an oily substance.

The peptide may also be employed in combination with a toxic ion as hereinabove described in the form of an oral composition for oral hygiene. Such a composition may be incorporated into a wide variety of compositions and materials used for oral hygiene purposes, which include, but are not limited to, toothpastes, mouthwashes, tooth gels, and tooth powders. Such composition may thus be used to treat or prevent periodontal disease, to prevent or reduce plaque, and/or to prevent or treat or reduce dental caries. The peptide and toxic ion may be used to inhibit, prevent, or destroy the growth of *Streptococcus mutans*, which is associated with dental caries and periodontal disease.

Numerous modifications and variations of the present invention are possible in light of the above teachings and, therefore, within the scope of the accompanying claims, the invention may be practiced other than as particularly described.

What is claimed is:
1. An antimicrobial peptide selected from the class consisting of:
  (SEQ ID NO:1);
  (SEQ ID NO:2);
  (SEQ ID NO:3);
  (SEQ ID NO:4);
  (SEQ ID NO:5); and
  (SEQ ID NO:6).

2. A process for inhibiting growth of a target cell, virus, or virally-infected cell comprising administering to a host an antimicrobial peptide selected from the class consisting of:
  (SEQ ID NO:1);
  (SEQ ID NO:2);
  (SEQ ID NO:3);
  (SEQ ID NO:4);
  (SEQ ID NO:5); and
  (SEQ ID NO:6).

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
( A ) LENGTH: 20 amino acids
( B ) TYPE: amino acid
( C ) STRANDEDNESS:
( D ) TOPOLOGY: linear ( i i ) MOLECULE TYPE: peptide ( v i ) ORIGINAL SOURCE:
( A ) ORGANISM: Rana catesbiana ( i x ) FEATURE:
( D ) OTHER INFORMATION: disulfide bond between Cys14 and Cys20

( x i ) SEQUENCE DESCRIPTION: SEQ ID NO:1:

```
Phe Leu Gly Gly Leu Ile Lys Ile Val Pro
                 5                    10
Ala Met Ile Cys Ala Val Thr Lys Lys Cys
                15                    20
```

( 2 ) INFORMATION FOR SEQ ID NO:2:

( i ) SEQUENCE CHARACTERISTICS:
        ( A ) LENGTH: 20 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: disulfide bond between Cys14 and Cys20

( x i ) SEQUENCE DESCRIPTION: SEQ ID NO:2:

```
Gly Leu Gly Gly Leu Ile Lys Ile Val Pro
                 5                    10
Ala Met Ile Cys Ala Val Thr Lys Lys Cys
                15                    20
```

( 2 ) INFORMATION FOR SEQ ID NO:3:

( i ) SEQUENCE CHARACTERISTICS:
        ( A ) LENGTH: 20 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: disulfide bond between Cys14 and Cys20

( x i ) SEQUENCE DESCRIPTION: SEQ ID NO:3:

```
Gly Leu Gly Lys Leu Ile Lys Ile Val Pro
                 5                    10
Ala Met Ile Cys Ala Val Thr Lys Lys Cys
                15                    20
```

( 2 ) INFORMATION FOR SEQ ID NO:4:

( i ) SEQUENCE CHARACTERISTICS:
        ( A ) LENGTH: 20 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: disulfide bond between Cys14 and Cys20

( x i ) SEQUENCE DESCRIPTION: SEQ ID NO:4:

```
Phe Leu Gly Gly Leu Ile Lys Ile Val Gly
                 5                    10
Ala Met Ile Cys Ala Val Thr Lys Lys Cys
                15                    20
```

( 2 ) INFORMATION FOR SEQ ID NO:5:

( i ) SEQUENCE CHARACTERISTICS:
        ( A ) LENGTH: 20 amino acids
        ( B ) TYPE: amino acid
        ( C ) STRANDEDNESS:
        ( D ) TOPOLOGY: linear ( i i ) MOLECULE TYPE: peptide -continued (ix) FEATURE:
  (D) OTHER INFORMATION: disulfide bond between Cys14 and Cys20

(xi) SEQUENCE DESCRIPTION: SEQ ID NO:5:

Phe Leu Gly Gly Leu Ile Lys Ile Val Pro
                  5                      10
Ala Leu Ile Cys Ala Val Thr Lys Lys Cys
               15                        20

(2) INFORMATION FOR SEQ ID NO:6:

(i) SEQUENCE CHARACTERISTICS:
    (A) LENGTH: 20 amino acids
    (B) TYPE: amino acid
    (C) STRANDEDNESS:
    (D) TOPOLOGY: linear (ii) MOLECULE TYPE: peptide (ix) FEATURE:
    (D) OTHER INFORMATION: disulfide bond between Cys14 and Cys20

(xi) SEQUENCE DESCRIPTION: SEQ ID NO:6:

Phe Leu Gly Gly Leu Ile Lys Ile Val Pro
                  5                      10
Ala Ile Ile Cys Ala Val Thr Lys Lys Cys
               15                        20